United States Patent
Jung et al.

(10) Patent No.: US 11,701,514 B2
(45) Date of Patent: Jul. 18, 2023

(54) SEGMENTED RING ELECTRODE

(71) Applicant: Heraeus Deutschland GmbH & Co. KG, Hanau (DE)

(72) Inventors: Markus Jung, Hanau (DE); Katharina Musiol, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 485 days.

(21) Appl. No.: 16/984,410

(22) Filed: Aug. 4, 2020

(65) Prior Publication Data
US 2021/0038882 A1    Feb. 11, 2021

(30) Foreign Application Priority Data

Aug. 5, 2019 (DE) ............. 10 2019 211 689.2

(51) Int. Cl.
| | | |
|---|---|---|
| A61B 5/24 | (2021.01) | |
| A61N 1/05 | (2006.01) | |
| B29C 70/84 | (2006.01) | |
| B29L 31/00 | (2006.01) | |

(52) U.S. Cl.
CPC ............ *A61N 1/0534* (2013.01); *A61B 5/24* (2021.01); *B29C 70/84* (2013.01); *B29L 2031/753* (2013.01)

(58) Field of Classification Search
CPC ............ A61N 1/0534; A61N 1/36182; A61N 1/0551; A61N 1/05; A61B 5/24; A61B 2562/125; B29C 70/84; B29L 2031/753
See application file for complete search history.

(56) References Cited

U.S. PATENT DOCUMENTS

| | | |
|---|---|---|
| 4,925,621 A | 5/1990 | Muth et al. |
| 9,566,747 B2 | 2/2017 | Romero et al. |
| 2006/0173262 A1* | 8/2006 | Hegland ............ B29C 45/14639 600/373 |
| 2011/0072659 A1 | 3/2011 | Swanson et al. |
| 2011/0130803 A1 | 6/2011 | McDonald |
| 2011/0245903 A1 | 10/2011 | Schulte et al. |

(Continued)

FOREIGN PATENT DOCUMENTS

| | | |
|---|---|---|
| EP | 0318248 | 5/1989 |
| EP | 3024535 | 6/2016 |

(Continued)

*Primary Examiner* — Ankit D Tejani
*Assistant Examiner* — Joshua Brendon Solomon
(74) *Attorney, Agent, or Firm* — Dicke, Billig & Czaja, PLLC (57) ABSTRACT

One aspect is a process for producing a segmented electrode, including providing a pipe made of metal having an outer side and an inner side, wherein the inner side of the pipe forms a hollow space. A support structure is arranged in the hollow space, so that the support structure mechanically stabilizes the pipe. Intermediate spaces are formed in the pipe, which define a plurality of segments in the pipe. An electrically insulating material is introduced into the intermediate spaces and thus forming electrically insulating areas, wherein a boundary layer is in each case defined between the segments and the areas. The pipe is cut so that several segmented ring-shaped electrodes are formed therefrom. The support structure is removed from the pipe.

15 Claims, 3 Drawing Sheets

(56) References Cited

U.S. PATENT DOCUMENTS

| | | |
|---|---|---|
| 2014/0296951 A1 | 10/2014 | Vetter et al. |
| 2015/0018915 A1 | 1/2015 | Leven |
| 2016/0208114 A1 | 7/2016 | Hendricks et al. |
| 2018/0042506 A1 | 2/2018 | Locke et al. |
| 2019/0223949 A1* | 7/2019 | Coates .............. A61B 18/1492 |

FOREIGN PATENT DOCUMENTS

| | | |
|---|---|---|
| EP | 3284509 | 2/2018 |
| WO | 2015/031265 | 3/2015 |

* cited by examiner

SEGMENTED RING ELECTRODE

CROSS-REFERENCE TO RELATED APPLICATION

This Utility Patent Application claims priority to German Application No. 10 2019 211 689.2 filed on Aug. 5, 2019, which is incorporated herein by reference.

TECHNICAL FIELD

One embodiment relates to a process for producing a segmented electrode, and an electrode, which can be produced according to this process. An electrode of this type is in one embodiment for the medical application. Possible applications are, for example, pacemakers and neuromodulation. The electrodes according to one embodiment can be used, for example, in connection with leads and pulse generators.

BACKGROUND

Electrodes, which have a plurality of segments, which can be electrically controlled independently of one another, are in one embodiment in the medical technology. As a result, it is possible to simultaneously output or receive electrical signals, which are independent of one another, at different points of the human or animal body.

It is a technical challenge in the production of a segmented electrode of this type to separate the individual segments from one another and to simultaneously ensure the stability of the overall construction. In the prior art, external support structures, which consist of the same material as the segments, usually a biocompatible metal, are used to stabilize the overall construction. Support structures of this type increase the material usage in the production and have to be removed again in a labor-intensive and time-consuming manner.

EP3284509 A1 describes an injection molding process, which uses an external support structure of this type. This support structure connects the individual segments to one another in order to stabilize them during the production process. This support structure is removed again by means of centerless grinding. The process described there is furthermore based on injection molding technology, which requires a specifically adapted tool.

As a result, only a single electrode can in each case be produced per workpiece. This process is furthermore not very flexible, i.e. it is difficult to make smaller adaptations, for example when different electrodes are to each be manufactured in small quantities.

EP3024535 B1 describes a similar process, in the case of which a sacrificial ring serves as external support structure. A coating with polymer only occurs in the final assembly step of the electrode.

The above-described processes of the prior art are often problematic when components with small dimensions and/or complex shape are to be produced. Thin film technologies, which are described, for example, in US20140296951 A1, often do not provide a good long-term stability of the produced components.

SUMMARY

It is the object of various embodiments to solve the above-described and further problems of the prior art. The process according to one embodiment can offer, for example, advantages with regard to material saving, shorter processing time, and flexibility. Special embodiments offer further advantages, which are described in more detail below herein. They can be, for example, an improved stability or improved electrical properties.

These objects are solved by the processes and systems described herein, in particular those, which are described in the patent claims.

Exemplary embodiments will be described below.

Embodiment 1 is a process for producing a segmented electrode, including the following steps:
 a. providing a pipe made of metal having an outer side and an inner side, wherein the inner side of the pipe forms a hollow space,
 b. arranging a support structure in the hollow space, so that the support structure mechanically stabilizes the pipe,
 c. forming intermediate spaces in the pipe, which define a plurality of segments in the pipe,
 d. introducing an electrically insulating material into the intermediate spaces and thus forming electrically insulating areas, wherein a boundary layer is in each case defined between the segments and the areas,
 e. cutting the pipe, so that several segmented ring-shaped electrodes are formed therefrom,
 f. removing the support structure from the pipe.

The process according to embodiment 1, wherein the support structure and the pipe have different materials or consist of different materials.

The process according to embodiment 3, wherein the support structure contains a base metal, preferably iron, molybdenum, magnesium, copper, aluminum, tin, zinc, nickel or an alloy thereof.

The process according to embodiment 3 or 4, wherein the step of removing the support structure from the pipe includes a chemical process, preferably an etching process.

The process according to any one of the preceding embodiments, wherein the outer side of the pipe is additionally structured to form a structure on the outer side of the pipe, and wherein the structure is configured to provide for the electrical contacting of the formed ring electrode.

The process according to embodiment 5, wherein the structure is an opening, which connects the outer side to the inner side of the pipe.

The process according to any one of the preceding embodiments, wherein the outer side of the pipe is additionally coated.

The process according to any one of the preceding embodiments, wherein the electrically insulating areas are formed by means of extrusion or dip coating.

The process according to any one of the preceding embodiments, wherein the electrically insulating areas have an extrudable polymer, preferably ETFE, PTFE, PFA, FEP, TPU or PEEK or consist thereof.

The process according to any one of the preceding embodiments, wherein the segments are each structured at the boundary layer, so that the connection between the segments and the electrically insulating areas is improved.

The process according to any one of the preceding embodiments, wherein the segments and the electrically insulating areas are in each case connected to one another by means of a substance-to-substance bond or in a positive (i.e. form-fit) manner by liquefying the electrically insulating material.

The process according to any one of the preceding embodiments, wherein the process steps are performed in the order a, b, c, d, e, f or a, b, c, d, f, e.

The process according to any one of embodiments 1 to 12, wherein the support structure is a part of a device, which is configured to form the pipe of several wires.

The process according to embodiment 13, including the following steps:
  a. providing a plurality of wires,
  b. inserting the wires into the device, wherein the device has a support structure,
  c. assembling the wires to form a pipe with the help of the device, wherein segments, which are each separated from one another by means of intermediate spaces, are in each case formed in the pipe made of the wires, wherein the support structure mechanically stabilizes the pipe,
  d. filling the intermediate spaces with an electrically insulating material, so that electrically insulating areas are in each case formed from the material between the segments,
  e. removing the support structure from the pipe,
  f. cutting the pipe, so that several ring electrodes are formed therefrom.

A ring electrode, produced by means of a process according to any one of the preceding embodiments.

A medical device having a ring electrode according to embodiment 15, wherein the medical device is configured to output an electrical signal to the human body or to receive an electrical signal from the human body with the help of the ring electrode.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

With regard to the embodiments described herein, the elements of which "have", "include" or "comprise" a certain feature (e.g. a material), a further embodiment will generally always be considered, in which the respective element consists only of the feature, i.e. does not include any further components. The terms "have" and "comprise" are used synonymously herein, unless otherwise specified.

When an element is referred to in the singular form in an embodiment, an embodiment is likewise considered, in the case of which several of these elements are present.

Unless otherwise specified or unambiguously ruled out from the context, it is generally possible and is hereby unambiguously considered that features of different embodiments can also be present in the other embodiments described herein. It is generally likewise considered that all features, which are described herein in connection with a process, are also applicable for the products and devices described herein. Merely for the sake of conciseness, all of these considered combinations will not be listed explicitly in all cases. Technical solutions, which are known to be equivalent to the features described herein, are contemplated to be included in the scope of one embodiment.

A first aspect relates to a process for producing a segmented electrode, which includes the following steps:
  a. providing a pipe made of metal having an outer side and an inner side, wherein the inner side of the pipe forms a hollow space,
  b. arranging a support structure in the hollow space, so that the support structure mechanically stabilizes the pipe,
  c. forming intermediate spaces in the pipe, which define a plurality of segments in the pipe,
  d. introducing an electrically insulating material into the intermediate spaces and thus forming electrically insulating areas,
  wherein a boundary layer is in each case defined between the segments and the areas,
  e. cutting the pipe, so that several segmented ring-shaped electrodes are formed therefrom,
  f. removing the support structure from the pipe.

These process steps can generally take place in a different order, they can be performed, for example, in the order a, b, c, d, e, for a, b, c, d, f, e. Instead of steps a and b, a pipe comprising an already existing internal support structure, for example a metal core, can also be provided directly.

The pipe is an elongate body, for example made of metal. The pipe has an outer side and an inner side. The inner side of the pipe defines a hollow space in the interior of the pipe. It is likewise considered that pipes can also be made of further suitable materials, which, as is well known, are suitable for medical electrodes and which are electroconductive. The pipe in one embodiment has a biocompatible material. In particular the surface of the outer side of the pipe, which establishes contact with the body in the finished electrode, should have a surface made of a biocompatible material. In one embodiment, the pipe consists completely of a biocompatible material, for example a biocompatible metal. Suitable biocompatible metals are known in the subject area, for example Pt, Ir, Ta, Pd, Ti, Fe, Au, Mo, Nb, W, Ni, Ti or a mixture or alloy thereof, respectively. In some embodiments, the pipe has one of the alloys MP35, PtIr10, PtIr20, 316L, 301, 304 or nitinol, or consists thereof. The pipe can also include multi-layer material systems. In some embodiments, the pipe consists of one or several of these materials.

MP35 is a curable alloy on the basis of nickel-cobalt. A variation of MP35 is described in the industrial standard ASTM F562-13. In one embodiment, MP35 is an alloy, which includes 33 to 37% of Co, 19 to 21% of Cr, 9 to 11% of Mo, and 33 to 37% of Ni. PtIr10 is an alloy of 88 to 92% of platinum and 8 to 12% of iridium.

PtIr20 is an alloy of 78 to 82% of platinum and 18 to 22% of iridium.

316L is an acid-resistant CrNiMo austenitic steel with approx. 17% of Cr; approx. 12% of Ni, and at least 2.0% of Mo. A variation of 316L is described in the industrial standard 10088-2. In one embodiment, 316L is an alloy, which includes 16.5 to 18.5% of Cr; 2 to 2.5% of Mo, and 10 to 13% of Ni.

301 is a chromium nickel steel with a high corrosion resistance. A variation of 301 is described in the industrial standard DIN 1.4310. In one embodiment, 301 is an alloy, which includes 16 to 18% of Cr and 6 to 8% of Ni.

304 is an austenitic, acid-resistant 18/10 Cr-Ni steel, which is described, for example, in the manufacturing standards ASTM A213, ASTM A269, ASTM A312 or ASTM A632. 304 usually contains 8-10.5% of nickel, 18-20% of chromium, up to 2% of manganese, and up to 0.08% of carbon. 304L, which contains up to 12% by weight of nickel, is a variation of 304.

Nitinol is a nickel-titanium alloy with shape memory with an orderly cubic crystal structure and a nickel portion of approximately 55%, wherein the remaining portion consists of titanium. Nitinol has good properties with respect to biocompatibility and corrosion resistance. Unless otherwise specified, all percentages herein are to be understood as percentage by mass (% by weight).

The pipe can be made of a metal wire, for example by means of drawing processes, which are known in the prior art. The pipe can generally be produced by means of each common metal working process. An injection molding process, for example, can also be used. When the pipe consists of a material other than a metal, other processes may be suitable, which are known to the person of skill in the art to form this material.

In one embodiment, the pipe can be assembled of several metal wires, as is described herein in more detail below. These metal wires can consist of the same materials, as it is described above for the pipe.

A support structure is introduced into the hollow space of the pipe. The support structure can in one embodiment fill the hollow space completely. The support structure can be a metal core, for example. Due to its structure and/or material properties, the support structure should in one embodiment be designed in such a way that it can be removed easily from the hollow space of the pipe again, as is further described below herein. The support structure can consist of a different material than the pipe. This is advantageous in one embodiment when the support structure is removed by means of a chemical process, as will be described in more detail below. The support structure can include a base metal. Iron, molybdenum, magnesium, copper, aluminum, tin, zinc, nickel, or an alloy, which contains one or several of these metals, are suitable metals for use in the support structure. Iron-nickel, brass or bronze are examples for an alloy of this type. In the alternative, the support structure can also include a polymer. PEEK, for example, is a suitable polymer.

The support structure is arranged in the hollow space in such a way that it mechanically stabilizes the pipe. This has the effect that the individual segments do not move relative to one another in the further course of the process described below. Due to the interior support structure, an exterior support structure, which is used in the prior art, can be forgone.

In a further step of the process, intermediate spaces are molded in the pipe, so that several segments emerge from the jacket of the pipe, i.e. the intermediate spaces define a plurality of segments. These intermediate spaces are molded in such a way that the individual segments are not electrically connected to one another in the formed electrode. After the formation of the intermediate spaces, the segments are in one embodiment only still connected to one another via the support structure. This provides for an individual electrical addressability of the individual segments, i.e. the individual segments can in each case be electrically controlled independently of one another, so that the individual electrical signals do not directly influence one another. A crosstalk between the individual segments thus essentially does not take place.

All of the shaping or separating processes, which are suitable for the corresponding material, can generally be used to mold the intermediate spaces. A pultrusion process or a chip removal process, for example a milling process or a laser-based manufacturing process can be used, for example, in particular for metals. The pipe can be drawn, for example, together with the support structure located therein, when the materials of the pipe and of the support structure are cold-workable.

In a further process step, the intermediate spaces between the individual segments are filled with an electrically insulating material, i.e. an electrically insulating material is introduced into the intermediate spaces. Electrically insulating areas are thus formed between the individual segments. With the surface of the individual segments, the electrically insulating material thereby in each case defines a boundary layer. The electrically insulating material in one embodiment fills the intermediate spaces completely, so that the electrically insulating areas mechanically stabilize the individual segments. This stabilizing effect is important in one embodiment, so that the structure of the segmented electrode is also maintained when the support structure is removed again in the further course of the process. In the absence of the support structure and of the electrically insulating areas, the overall construction of the segmented electrode would not be mechanically stable.

The electrically insulating material can be introduced into the intermediate spaces with the help of different processes. Extrusion, dip coating or injection molding are examples for suitable processes. Other coating processes can also be used. The electrically insulating material can be systematically introduced into the intermediate spaces with the help of an extrusion process, so that the remaining surfaces, in particular the outer side of the pipe or of the segments, respectively, are not coated with the electrically insulating material.

The electrically insulating material can be a polymer, for example ETFE, PTFE, PFA, FEP, TPU or PEEK. The polymer is in one embodiment suitable to be introduced into the intermediate spaces by means of an extrusion process. The electrically insulating material is in one embodiment medically compatible. The electrically insulating material can also be a medically compatible silicon.

In the alternative, the electrically insulating material can be a ceramic, for example on the basis of $Al_2O_3$ or $ZrO_2$. The ceramic is in one embodiment introduced into the intermediate spaces between the segments in the form of a deformable ceramic-containing compound by means of extrusion or injection molding.

After the coating, excess parts of the electrically insulating material can optionally be removed, for example by means of laser ablation. A smoother and/or more homogenous surface structure can be attained thereby.

After the electrically insulating material is introduced into the intermediate spaces and electrically insulating areas have formed, which provide the composite with a sufficient stability, the pipe can be cut, so that several ring-shaped segmented electrodes are formed therefrom. Each process, which is common in the subject area, for example mechanical cutting processes or laser cutting processes, can be used for this purpose.

Before or after the step of cutting, the support structure is removed from the pipe. When the support structure is removed before the cutting, the cutting can take place with less mechanical force or laser power, respectively, or higher speed. When the support structure is still present during the cutting, a deformation of the pipe can be avoided during the cutting, in particular during the mechanical cutting.

When the material of the pipe and of the support structure are selected accordingly, the support structure can be removed by means of a chemical process. This can be, for example, a wet-chemical etching process or a plasma etching process. Corresponding material and etching systems are known in the subject area. The pipe can be made, for example, of a precious metal or of a corrosion-resistant alloy, and the support structure can be made of a base metal or of a base alloy, so that the support structure can be selectively removed by means of a suitable etching solution, for example a strong acid.

Sulfuric acid, hydrochloric acid, nitric acid, permonosulfuric acid are examples for suitable acids. Iron chloride and copper sulfate are further suitable etching chemicals.

In the alternative, the support structure can be removed with the help of mechanical processes in the case of suitable selection of the material and/or of the structure. In one embodiment, the conductive segments and insulating intermediate spaces can be made of materials with high melting point, and the support structure can be made of a material with lower melting point, so that the support structure melts or evaporates by means of heating and can thus be removed.

By removing the support structure, an empty hollow space is formed again in the interior of the pipe, i.e. solid material is no longer present in the hollow space.

The pipe can furthermore be structured on the outer side. For example a structure, which is configured to provide for the electrical contacting of the formed ring electrode, can be formed in this way. A structure of this type can be, for example, an opening, which connects the outer side of the pipe to the inner side of the pipe. A continuous opening of this type provides for a stable connection to an electrical conductor, for example a line wire. For this purpose, the conductor can be guided through the opening and can subsequently be connected to the pipe or the electrode, respectively, in a non-positive (i.e. force-fit) and/or positive (i.e. form-fit) manner. For example, the free end of a conductor can be clamped into the opening and/or can be welded inside or to it.

With regard to this, reference is made to the application DE102018221355 by the same applicant, the content of which is hereby incorporated by reference in this application. It is expressly intended that protection is sought in connection with the present embodiments for the structures described in DE102018221355 for connecting the pipe to a line wire.

In one embodiment, the material of the pipe surrounds the opening in its entirety. This means that the opening is arranged in the pipe such that the line wire guided therein cannot be moved laterally out of the opening, without first moving it along the longitudinal axis of the opening. A stable and fatigue-free fastening of the conductor to the pipe is thus made possible. The opening can be arranged, for example, essentially centrally in the wall of the pipe, thus in the jacket surface of the electrode or of the pipe, respectively. The connection between the line wire and the pipe and the electrode produced therefrom is thus more stable and fatigue-free. In one embodiment, the opening thus does not touch the outer edge of the electrode or of the pipe, respectively. In another embodiment, the conductor is fastened to the edge of the electrode. In one embodiment, the opening extends continuously from the inner side to the outer side. This makes it possible to guide a free end of the conductor completely through the jacket surface of the pipe. This provides for a particularly stable fastening of the conductor to the pipe. The embodiment of this fastening can thus also be attained more easily. The electrical conductor can thereby be guided through the opening from the inner side to the outer side, so that an end of the conductor is consistently flush with the outer side.

In one embodiment, the opening has a varying diameter. The opening can be conical, for example. The opening can in one embodiment have a smaller diameter on the outer side than on the inner side. When the opening tapers from the inner side to the outer side of the pipe, in one embodiment tapers continuously, this can serve, for example, for the improved guidance of the conductor through the opening. The opening is guided transversely to the longitudinal axis of the pipe. The opening can either extend perpendicular to the longitudinal axis of the hollow space of the pipe or at a different angle thereto. "Transversely" means herein that two axes do not run parallel to one another, are thus arranged at an angle to one another, which differs from 0° or 180°, for example an angle of 1° to 179°. The longitudinal axis of the opening can be arranged, for example, at an angle of 1° to 179° to the longitudinal axis of the hollow space of the pipe. In one embodiment, the angle is 2° to 188°, 5° to 185°, or 10° to 170°. In one embodiment, the angle is 20° to 160°. In one embodiment, the angle is 40° to 140°. In one embodiment, the angle is 80° to 110°.

On its surface, i.e. on the outer side or the inner side of the pipe, the opening can have different shapes. In one embodiment, the opening is essentially circular. In a further embodiment, the opening on the surface is essentially elliptical. In a further embodiment, the opening on the surface has the shape of a rounded triangle, the tip of which is arranged in the direction of the free end of the conductor.

In one embodiment, the opening on the surface has a diameter perpendicular to its longitudinal extension of less than 0.2 mm. In a further embodiment, the diameter of the opening is smaller than 0.1 mm. The diameter is at least 10 micrometers. In one embodiment, the diameter of the opening is larger than the diameter of the conductor. In one embodiment, the diameter of the opening is larger than the diameter of the conductor or larger than the diameter of the thinnest wire of the conductor.

In one embodiment, the pipe, and thus also the electrode formed therefrom, contains several openings. These openings can extend essentially parallel to one another or at an angle to one another with respect to their respective longitudinal axis. The longitudinal axis of the opening runs from the inner side to the outer side of the pipe.

In one embodiment, the opening has a stop for holding one end of the conductor, in one embodiment the free end. The conductor can be guided in such a way, for example, that it abuts against the stop. A better fixation of the conductor can be attained thereby. In one embodiment, the electrode formed of the pipe contains a further opening, for example a total of 2, 3, 4, 5, 6, 10 or more than 10 openings.

Connection of the Pipe to the Conductor

A connection by means of a substance-to-substance bond can be attained, for example, by means of welding, brazing, or soft soldering. In one embodiment, the substance-to-substance bond is a welded connection. The welded connection can be attained, for example, by means of laser welding. By fusing the conductor as part of the welding, the opening in the pipe can be closed completely. The penetration of fluids or another contaminations into the opening can be avoided thereby. In addition, sharp edges or burrs of the outer side of the opening can be covered and can thus be smoothed.

In one embodiment, the electrical conductor is connected in a non-positive (i.e. force-fit) manner to the pipe within the opening. This non-positive connection can be attained by clamping by means of tweezers, crimping or swaging (drop-forging) or other mechanical swaging processes, which are known in the art. Some suitable processes are described in EP318248A1. Comparable processes, which are known to the person of skill in the art in this context, can also be used.

In one embodiment, the electrical conductor is directly connected by means of a substance-to-substance bond to the pipe within the opening. In one embodiment, the electrical conductor is directly connected in a non-positive (i.e. force-fit) manner to the pipe within the opening. In one embodiment, the electrical conductor is directly connected by means of a substance-to-substance bond as well as directly in a non-positive manner to the pipe within the opening. In one embodiment, the electrical conductor is directly connected by means of a substance-to-substance bond, but not in a non-positive manner, to the pipe within the opening.

The electrical conductor can furthermore also be connected in a positive (i.e. form-fit) manner to the pipe within the opening. In one embodiment, the electrical conductor is directly connected in a positive manner to the pipe within the opening.

In one embodiment, the electrical conductor is connected by means of a substance-to-substance bond, but not in a non-positive manner, to the pipe. The electrical conductor can also be connected exclusively by means of a substance-to-substance bond to the pipe. A substance-to-substance bond is in one embodiment a welded connection. Due to a complete substance-to-substance bond, a deformation of the pipe is avoided and a very stable, permanent and highly conductive connection is simultaneously attained between the conductor and the electrode. This is particularly advantageous in one embodiment when the electrode has a certain surface property and is to also maintain the latter after being contacted with the conductor. For example particularly smooth electrode surfaces, which are precisely defined in their geometry, can thus be attained.

In the alternative or in addition to the above-described opening, the electrode can have a structure in the shape of a groove. A line wire can be connected in a non-positive and/or positive manner to the pipe in this way, without the line wire having to have a free end for this purpose. For this purpose, the line wire can be clamped and/or welded into the groove. With regard to this, reference is made to the application DE102018221635 by the same applicant, the content of which is hereby added into this application. It is expressly intended that protection is sought in connection with the present embodiments for the structures described in DE102018221635 for connecting the pipe to a line wire.

A structure can be created, for example, by means of laser drilling, spark erosion or chip removal processes. In one embodiment, several segments have a structure, as it is described above. In one embodiment, each of the segments has at least one structure of this type. Each segment is in one embodiment connected to another conductor by means of the structure. This makes it possible that each segment can be electrically addressed individually. Different electrical signals can be output or received by several segments independently of one another by means of a segmented electrode, in the case of which each segment can be electrically addressed individually, without these signals mutually influencing one another.

In one embodiment, signals can be output in different directions by different segments, or signals can be received from different directions. In one embodiment, the segments are configured and arranged to output signals in different directions, or to receive signals from different directions. In one embodiment, the segments are arranged at different circumferential positions of the pipe for this purpose. In one embodiment, the segments are arranged at different radial angles to the main axis of the rotor.

In one embodiment, the pipe can additionally be coated. The surface of the outer side of the pipe or the outer surface of the individual segments can in particular be coated. A coating of this type can improve, for example, the biocompatibility or the electrical properties of the electrode. A coating can effect a lower impedance or can improve the electrical contact between conductor and electrode, or the electrical contact to the body of a living being. TiN, Ir, $IrO_x$, Pt or conductive polymers, for example conductive polymers on the basis of thiophene, such as, for example, poly-3,4-ethylenedioxythiophene (PEDOT) or the conductive polymers described in WO/2015/031265 (incorporated completely herein by reference) can be used for a coating of this type. It is expressly intended that protection is sought in connection with the present embodiments for the conductive polymers on the basis of thiophene described in WO/2015/031265.

A coating with metals or alloys can be carried out, for example, by means of PVD, CVD or electrochemical separation.

In one embodiment, the boundary layer between the segments and the electrically insulating areas is structured, so that the connection between the segments and the electrically insulating areas is improved. For example elevations, depressions or undercuts at the segments can be created in the area of these boundary layers. In the alternative or in addition, the boundary layer can be roughened. Due to structures of this type and roughened surfaces, the surface of the boundary layers increases, so that the stability of the segmented electrode is improved, because a higher adhesive force acts between the segments and the electrically insulating areas. In one embodiment, the intermediate spaces, including the structures, are filled completely with the electrically insulating material. The connection of the segments to the electrically insulating areas can optionally be further improved by means of a further process step, for example by means of laser welding.

In one embodiment, the electrically insulating areas are connected by means of a substance-to-substance bond to the segments by liquefying the electrically insulating material. This means that the electrically insulating material is introduced in liquid form into the intermediate spaces between the segments, and subsequently solidifies there. The material of the segments remains unchanged thereby. In particular in connection with the above-described structuring of the boundary layer, the stability of the segmented electrode improves thereby, because the segments and the electrically insulating areas are connected more firmly to one another. In one embodiment, the segments and the electrically insulating areas are in each case connected to one another by means of a substance-to-substance bond by liquefying the electrically insulating material.

In one embodiment, the electrically insulating areas are connected in a positive manner to the segments. The positive connection is created by the meshing of a segment and of an electrically insulating area. Segment and electrically insulating area can thus not detach from one another even without an additional stabilizing force or structure. In one embodiment, segments and insulating areas have structures, which are complementary to one another and which provide for a positive connection to one another.

In a further embodiment, a process as described above is disclosed, wherein the support structure is part of a device, which is configured to form the pipe of several wires.

In a further embodiment, the process has the following steps:
a. providing a plurality of wires,
b. inserting the wires into the device, wherein the device has a support structure,
c. assembling the wires to form a pipe with the help of the device, wherein segments, which are each separated from one another by means of intermediate spaces, are in each case formed in the pipe made of the wires, wherein the support structure mechanically stabilizes the pipe,
d. filling the intermediate spaces with an electrically insulating material, so that electrically insulating areas are in each case formed from the material between the segments,
e. removing the support structure from the pipe,
f. cutting the pipe, so that several ring electrodes are formed therefrom.

A further aspect relates to an electrode, which is produced according to an above-described process. An electrode of this type can be characterized, for example, in that the electrically insulating areas and the segments are connected to one another more firmly than in the case of an electrode according to the prior art. In one embodiment, the electrode contains several segments, wherein each segment is connected to another conductor, for example with the help of a structure, as it is described above herein. This makes it possible that each segment can be electrically addressed individually. Different electrical signals can be output or received by several segments independently of one another by means of a segmented electrode, in the case of which each segment can be electrically addressed individually, without these signals mutually influencing one another.

In a further aspect, an electrical medical device is provided, having an electrode according to any one of the preceding aspects and embodiments thereof.

The electrical medical device can be, e.g., a lead, pulse generator, pacemaker, cardiac resynchronization device, sensor or stimulator. Leads are electrical lines, which can be used, for example, in medical applications, such as neuromodulation, cardiac stimulation, deep brain stimulation, spinal cord stimulation or gastric stimulation. In one embodiment, the lead is configured and/or arranged to be connected to a generator of an active implantable device. A lead can also be used in a medical device to receive an electrical signal. A stimulator is a medical device, which can have a physiological effect by outputting an electrical signal to the body of a living being. For example, a neurostimulator can effect an electrical signal in the nerve cell (e.g. an action potential) by outputting an electrical signal to a nerve cell.

A further embodiment relates to a microelectrode or a microelectrode array, which includes a system described herein.

A further aspect relates to a diagnostic method in or on the body of a living being, including the receiving of an electrical signal by means of the electrode described herein.

A further aspect relates to the use of the electrode described herein in a diagnostic method in or on the body of a living being, including the receiving of an electrical signal by means of the electrode.

A further aspect relates to a therapeutic method in or on the body of a living being, including the outputting of an electrical signal by means of the electrode described herein.

A further aspect relates to the use of the electrode described herein in a therapeutic method in or on the body of a living being, including the outputting of an electrical signal by means of the electrode.

The therapeutic method can include the outputting of an electrical signal to nerve cells or muscle cells in the area of an organ, for example heart, muscle, stomach or brain.

The diagnostic method can include the reception of an electrical signal from nerve cells or muscle cells in the area of an organ, for example heart, muscle or brain.

EXAMPLES

Embodiments will be further clarified below on the basis of examples, which, however, are not to be understood to be limiting. It becomes clear to the person of skill in the art that instead of the features described here, other equivalent means can be used in a similar way instead.

Figure 1A:
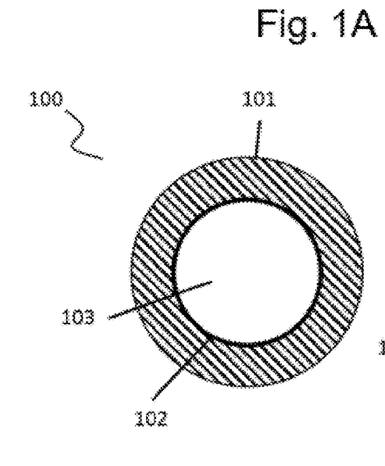
FIGS. 1A-1B illustrate a first step of the process described herein, in which a pipe made of metal is provided.
Figure 1B:
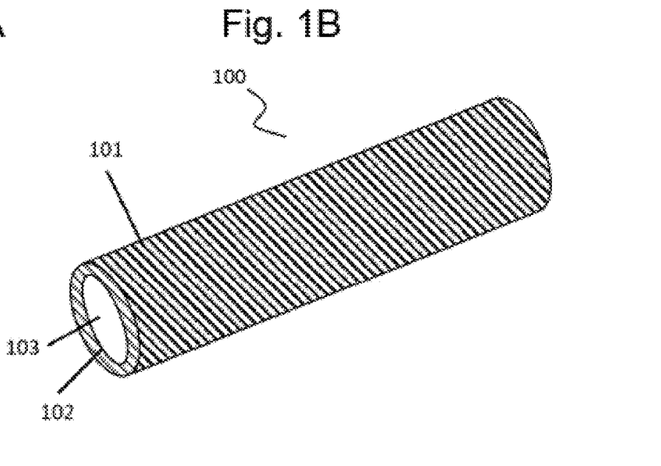

In a first step of the process described herein, a pipe 100 made of metal is provided, as shown in FIGS. 1A and 1B. FIG. 1A shows a cross section through the pipe, FIG. 1B shows a top view onto the pipe. The pipe has an outer side 101 and an inner side 102, wherein the inner side 102 of the pipe 100 forms a hollow space 103. The pipe 100 in one embodiment consists of a metal, as describe above herein. This metal can be a metal alloy. However, other suitable electroconductive, solid materials can also be used, which are described herein.

The pipe 100 can be assembled of several wires, as is also described in more detail herein.

Figure 2A:
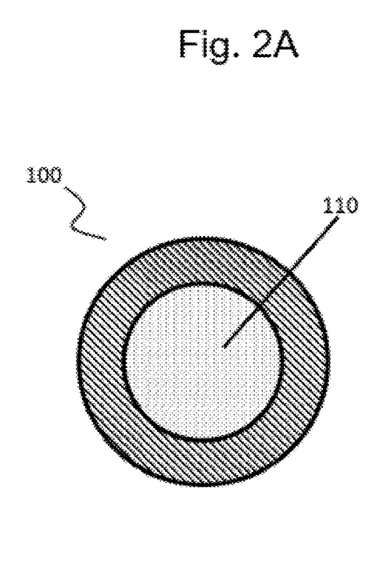
FIGS. 2A-2B illustrate a second step of the process, in which a support structure is arranged in the pipe.
Figure 2B:
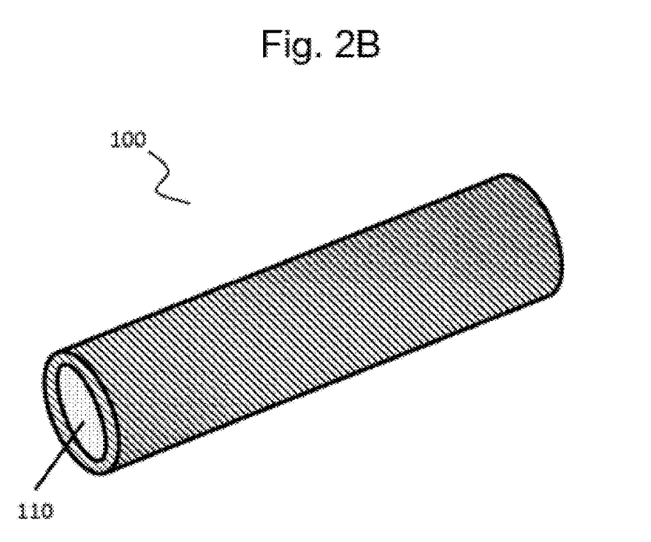

A support structure 103 is arranged in the hollow space 103 of the pipe 100, as it is shown in FIGS. 2A and 2B. FIG. 2A shows a cross section through a pipe 100, in which a support structure 110 is arranged. FIG. 2B shows a top view of the same process step. The support structure 110 in one embodiment fills the hollow space 103 completely, in order to attain a good mechanical stabilization of the pipe. The support structure 110 is in one embodiment formed of a different material than the pipe 100.

The support structure 110 differs from the pipe 100 in its mechanical and/or chemical properties, so that it is possible to remove the support structure 110 from the pipe 100, after the electrically insulating areas (FIGS. 4A, 140a, 140b, 140c) are introduced. The support structure 110 can in one embodiment be removed from the pipe 100 by means of a chemical process, without the pipe 100 changing thereby. This is possible, for example, by means of a material-selective etching process, as it is known in the subject area and as it is described above herein. The etching process can be a wet-chemical etching process or a plasma etching process. In another embodiment, the support structure 110 is removed mechanically. In one embodiment, mechanical as well as chemical processes are used to remove the support structure 110, for example an etching process in combination with ultrasound. In one embodiment, the support structure is removed by means of heating, for example in that the pipe is heated to a temperature, which is higher than the melting point of the material of the support structure 110, but lower than the melting point of the material of the pipe 100.

Figure 3A:
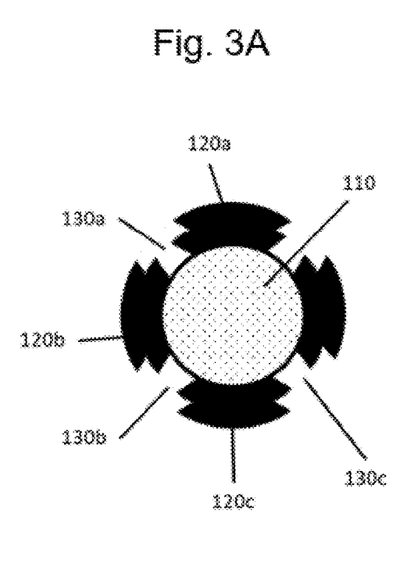
FIGS. 3A-3B illustrate a third step of the process, in which intermediate spaces are molded in the pipe.
Figure 3B:
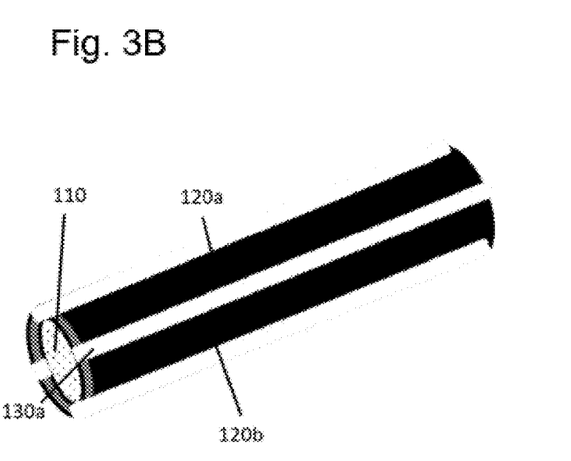

FIG. 3A (cross section) and FIG. 3B (top view) show a further step of the process, in which intermediate spaces 130a, 130b, 130c are formed in the pipe 100. This can take place, for example, with the help of a drawing process. The pipe, together with the contained support structure 110, can be subjected to the corresponding shaping process, for example a drawing process. The intermediate spaces 130a, 130b, 130c define a plurality of segments 120a, 120b, 120c in the pipe 100, i.e. the pipe 100 is divided into several areas, which are electrically insulated from one another, the segments 120a, 120b, 120c. After the formation of the intermediate spaces 130a, 130b, 130c, the segments 120a, 120b, 120c are in one embodiment only still connected to one another via the support structure 110.

Figures 4A, 4B:
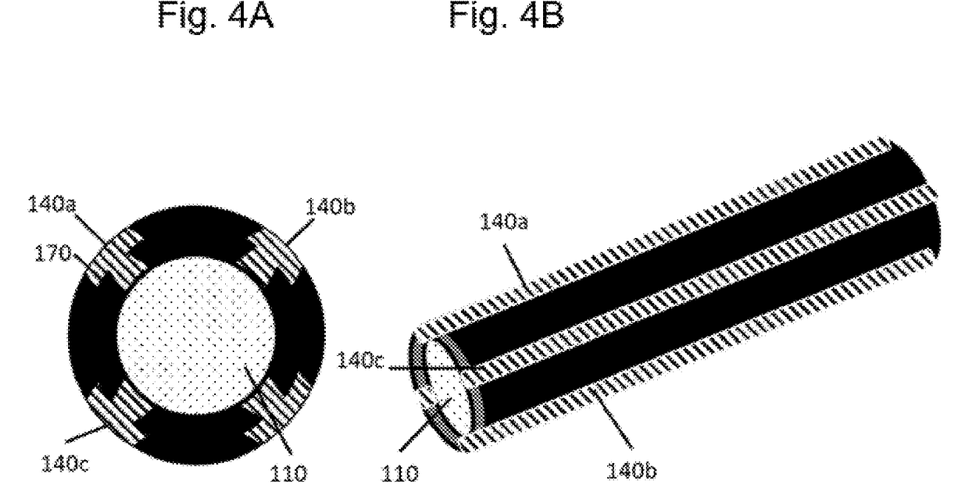
FIGS. 4A-4B illustrate a fourth step of the process, in which an electrically insulating material is introduced into the intermediate spaces.

FIG. 4A (cross section) and FIG. 4B (top view) show a further step of the process, in which an electrically insulating material is introduced into the intermediate spaces 130a, 130b, 130c. Electrically insulating areas 140a, 140b, 140c are formed thereby, which connect and mechanically stabilize the segments 120a, 120b, 120c, so that they are held in a firm position relative to one another.

Boundary layers 170 are in each case defined between the segments 120a, 120b, 120c and the electrically insulating areas 140a, 140b, 140c. The boundary layers 170 can have a structure, which improves the connection of the segments 120a, 120b, 120c to the electrically insulating material. This can be, for example, an elevation, depression and/or a step structure, as it is shown in FIG. 4A. The step structure can have an angle of 90° or an angle, which differs therefrom. In one embodiment, the step structure has an angle of less than 90 degrees, less than 75° or less than 45°, so that the segments 120a, 120b, 120c have pointy protrusions, which protrude into the electrically insulating areas 140a, 140b, 140c. The boundary layers 170 can also include undercuts. A stable connection to the electrically insulating areas 140a, 140b, 140c is made possible thereby. The electrically insulating material can be, for example, a meltable polymer, which is introduced into the spaces 130a, 130b, 130c in melted and in liquid form, for example by means of extrusion. It is made possible thereby that the molten polymer covers and encloses the boundary layers 170 completely, and that the intermediate spaces 130a, 130b, 130c are filled completely with the electrically insulating material. A strong adhesion between the electrically insulating material, for example a polymer, and the material of the segments 120a, 120b, 120c, for example a metal, takes place thereby. This connection can optionally be further improved by means of a further process step, for example by means of laser welding.

Figure 5:
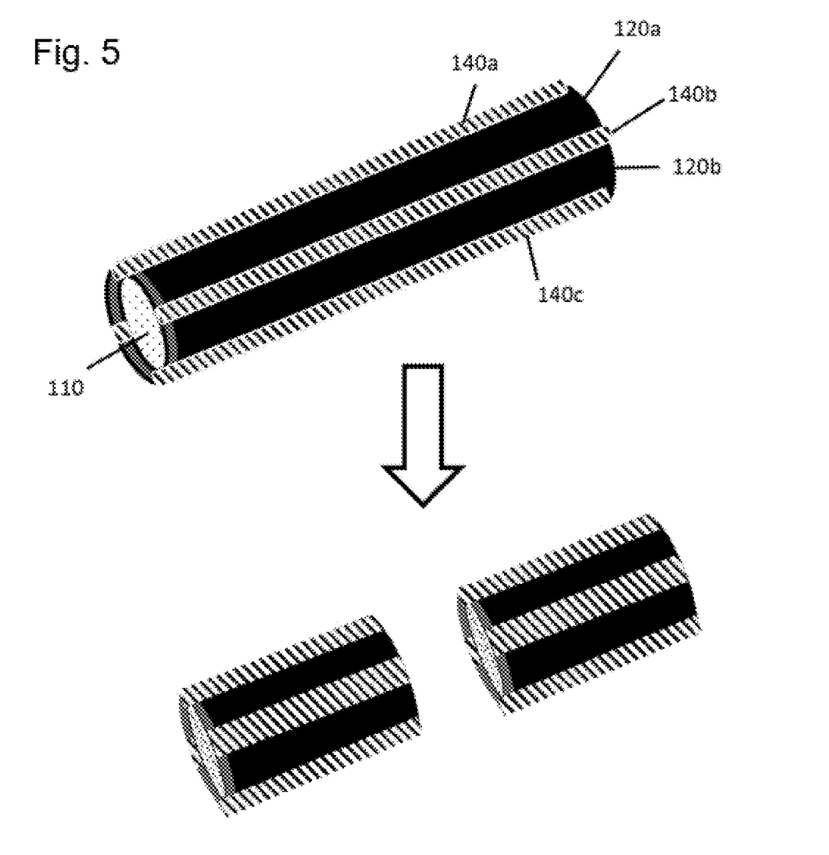
FIG. 5 illustrates a fifth step of the process, in which the pipe is cut to form several segmented electrodes therefrom.

FIG. 5 shows a further step of the process, wherein the pipe 100 is cut, so that several segmented ring-shaped electrodes are formed therefrom. The pipe 100 can be cut together with the support structure 110 contained therein, as it is shown in FIG. 5. In the alternative, it is possible to cut the pipe only after the removal of the support structure 110. By cutting the pipe 100 into several pieces, a plurality of electrodes can be produced by running through the process only once. Due to guisable selection of the distances, either similar electrodes or electrodes of different length can be produced from the same pipe 100. By varying the surface structure in different portions of the pipe 100, it is also possible to produce electrodes with different surface structure from the same pipe 100. For this purpose, the outer side 101 of the pipe 100 can be molded or coated differently at different locations before or after the cutting, as it is described in more detail above herein. The cutting of the pipe 100 can be performed, for example, by mechanical cutting (for example by means of a cutting knife, a milling cutter or an angle grinder) or laser cutting. The pipe 100 is thereby cut into several pieces in one embodiment at a right angle to the longitudinal axis of the pipe, so that a plurality of electrodes is created.

Before or after the cutting, the support structure 110 is removed from the pipe 100. For this purpose, the different material properties of the support structure 110 of the pipe 100 are in one embodiment utilized, i.e. a material-selective process is used. A material-selective etching process, for example, can be used, which is described in more detail above herein. An etching process of this type utilizes a chemical reaction with the material of the support structure 110, wherein the etching process is performed under conditions, under which the material of the pipe 100 is not attacked or is essentially not attacked and removed by the etching solution. Suitable material-selective etching processes are known for many common materials. A base metal, for example, can be removed with the help of a concentrated strong acid, without a precious metal being removed by the acid. Suitable parameters can optionally be determined with the help of simple tests, wherein acid concentration, temperature, and duration of the etching process are varied systematically. In the alternative, other suitable material-selective or non-material-selective processes can be used to remove support structure 110 from the pipe 100. The material of the support structure can for example be liquefied or burnt at an increased temperature, at which the material of the pipe 100 is still stable. For example, metals or alloys comprising different melting points, for example lead for the support structure 110 and platinum for the pipe 100 can be used for this purpose. Material-selective chemical processes represent a particularly effective method for removing the support structure 110.

Figure 6:
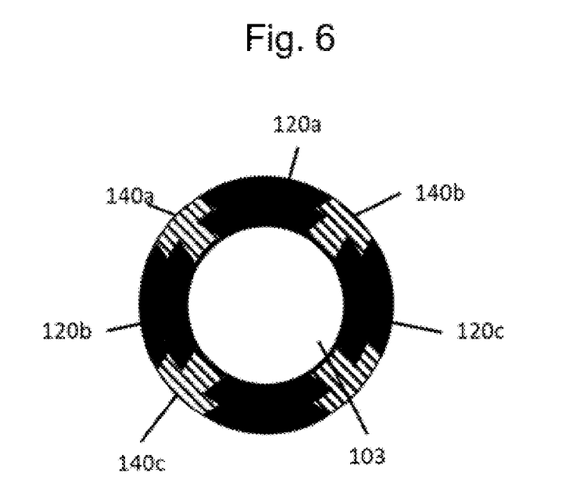
FIG. 6 illustrates a sixth step of the process, in which the support structure is removed from the pipe to form a segmented electrode comprising a hollow space.

An electrode produced by means of the process is shown in FIG. 6. The electrode in each case has several segments 120a, 120b, 120c, which are electrically insulated from one another and which are in each case connected to one another via electrically insulating areas 140a, 140b, 140c, located therebetween. The electrically insulated segments 120a, 120b 120c are connected to the electrically insulating areas 140a, 140b, 140c located therebetween in such a way that the electrode formed therefrom is mechanically stable even without the support structure 110, and the electrically insulated segments 120a, 120b 120c can in particular not be moved or removed relative to one another. The individual electrically insulated segments 120a, 120b, 120c can be electrically addressed independently of one another.

In one embodiment, the pipe 100 is assembled of several wires (not shown in the figures) in a device, wherein the device contains a support structure 110, which stabilizes the individual wires and thus holds them in a constant position to one another. The intermediate spaces 130a, 130b, 130c are also filled with an electrically insulating material in the same device, so that electrically insulating areas (see FIGS. 4A, 140a, 140b, 140c below) are formed from the material. The filling of the intermediate spaces 130a, 130b, 130c is carried out while the individual wires are stabilized in the device by means of the support structure 110.

The invention claimed is:

1. A process for producing a segmented electrode, comprising:
    a. providing a pipe made of metal having an outer side and an inner side, wherein the inner side of the pipe forms a hollow space;
    b. arranging a support structure in the hollow space, so that the support structure mechanically stabilizes the pipe;
    c. forming intermediate spaces in the pipe, which define a plurality of segments in the pipe;
    d. introducing an electrically insulating material into the intermediate spaces and thus forming electrically insulating areas,
        wherein a boundary layer is in each case defined between the segments and the areas;
    e. cutting the pipe, so that several segmented ring-shaped electrodes are formed therefrom; and
    f. removing the support structure from the pipe.

2. The process according to claim 1, wherein the support structure and the pipe have different materials or consist of different materials.

3. The process according to claim 1, wherein the support structure has a base metal, preferably iron, molybdenum, magnesium, copper, aluminum, tin, zinc, nickel or an alloy thereof or consists thereof.

4. The process according to claim 1, wherein the step of removing the support structure from the pipe includes a chemical process, preferably an etching process.

5. The process according to claim 1, wherein the outer side of the pipe is additionally structured to form a structure on the outer side of the pipe, and wherein the structure is configured to provide for the electrical contacting of the formed ring electrode.

6. The process according to claim 5, wherein the structure is an opening, which connects the outer side to the inner side of the pipe.

7. The process according to claim 1, wherein the outer side of the pipe is additionally coated.

8. The process according to claim 1, wherein the electrically insulating areas are formed by means of extrusion or dip coating.

9. The process according to claim 1, wherein the electrically insulating areas have an extrudable polymer, preferably ETFE, PTFE, PFA, FEP, TPU or PEEK or consist thereof.

10. The process according to claim 1, wherein the segments are each structured at the boundary layer, so that the connection between the segments and the electrically insulating areas is improved.

11. The process according to claim 1, wherein the segments and the electrically insulating areas are in each case connected to one another by means of a sub stance-to-sub stance bond or in a positive manner by liquefying the electrically insulating material.

12. The process according to claim 1, wherein the process steps are performed in the order a, b, c, d, e, for a, b, c, d, f, e.

13. The process according to claim 1, wherein the support structure is a part of a device, which is configured to form the pipe of several wires.

14. The process according to claim 13, including the following steps:
    a. providing a plurality of wires,
    b. inserting the wires into the device, wherein the device has a support structure,
    c. assembling the wires to form a pipe with the help of the device, wherein segments, which are each separated from one another by means of intermediate spaces, are in each case formed in the pipe made of the wires, wherein the support structure mechanically stabilizes the pipe,
    d. filling the intermediate spaces with an electrically insulating material, so that electrically insulating areas are in each case formed from the material between the segments,
    e. removing the support structure from the pipe,
    f. cutting the pipe, so that several ring electrodes are formed therefrom.

15. A segmented ring electrode, produced by a process according to claim 1.

* * * * *